United States Patent
Engl et al.

(10) Patent No.: US 10,238,550 B2
(45) Date of Patent: *Mar. 26, 2019

(54) WOUND CLEANING ASSEMBLY

(71) Applicant: L&R USA, INC., Milwaukee, WI (US)

(72) Inventors: Johannes Engl, Bildstein (AT); Robert Strohal, Feldkirch-Nofels (AT)

(73) Assignee: L&R USA, Inc., Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/919,858

(22) Filed: Mar. 13, 2018

(65) Prior Publication Data

US 2018/0200120 A1    Jul. 19, 2018

Related U.S. Application Data (63) Continuation of application No. 15/649,844, filed on Jul. 14, 2017, which is a continuation of application No. 14/790,398, filed on Jul. 2, 2015, now Pat. No. 9,713,553, which is a continuation of application No. 13/146,729, filed as application No. (Continued)

(30) Foreign Application Priority Data

Jan. 28, 2009 (AT) .................. A 145/2009

(51) Int. Cl.
  *A61F 13/00* (2006.01)
  *A61F 13/36* (2006.01)
  *A61B 17/32* (2006.01)

(52) U.S. Cl.
  CPC .............. *A61F 13/36* (2013.01); *A61F 13/00* (2013.01); *A61F 13/00017* (2013.01); *A61F 13/00021* (2013.01); *A61B 2017/320004* (2013.01); *A61B 2017/320012* (2013.01); *A61F 2013/00531* (2013.01)

(58) Field of Classification Search
  CPC .... A61F 13/36; A61F 13/00; A61F 13/00017; A61F 13/00021; A61F 2013/00531; A61F 13/00063; A61F 2013/00927
  See application file for complete search history.

(56) References Cited

U.S. PATENT DOCUMENTS 2,737,702 A    3/1956  Arnold et al.
3,561,441 A    2/1971  Lombardi
(Continued)

FOREIGN PATENT DOCUMENTS

CN    2276333    3/1998
CN    1259024    7/2000
(Continued)

OTHER PUBLICATIONS

Submission in EPO Opposition against EP 2 365 794 B1, dated Dec. 20, 2013.
(Continued)

*Primary Examiner* — Adam Marcetich
(74) *Attorney, Agent, or Firm* — Stinson Leonard Street LLP (57) ABSTRACT

A wound cleansing assembly, which includes or is a wound cleansing cloth (1), having at least one carrier layer (2) and threads (3) disposed on the carrier layer (2) and protruding from the carrier (2), preferably made exclusively of synthetic fibers, preferably plastic fibers.

14 Claims, 4 Drawing Sheets

Related U.S. Application Data

PCT/AT2010/000027 on Jan. 26, 2010, now abandoned.

(56) References Cited

U.S. PATENT DOCUMENTS

| | | | |
|---|---|---|---|
| 3,708,837 A | 1/1973 | Chiba | |
| 3,732,125 A | 5/1973 | Stroh | |
| 3,732,135 A | 5/1973 | Ernst et al. | |
| 4,244,074 A * | 1/1981 | Barcikowski | A46B 9/06 15/114 |
| 4,741,942 A * | 5/1988 | Swift | A46B 9/02 15/1.51 |
| 4,887,994 A | 12/1989 | Bedford | |
| 4,938,901 A | 7/1990 | Groitzsch | |
| 4,980,943 A | 1/1991 | Barber | |
| 5,040,260 A | 8/1991 | Michaels | |
| 5,484,427 A * | 1/1996 | Gibbons | A46B 11/063 119/603 |
| 5,623,941 A * | 4/1997 | Hedberg | A46B 3/02 600/569 |
| 5,697,920 A * | 12/1997 | Gibbons | A46B 11/063 604/289 |
| 5,921,251 A | 7/1999 | Joshi | |
| 5,953,783 A | 9/1999 | Hahn | |
| 6,017,351 A * | 1/2000 | Street | A61B 17/54 606/131 |
| 6,026,534 A | 2/2000 | Gonda et al. | |
| 6,378,161 B1 * | 4/2002 | Parry | G03G 15/2025 15/208 |
| 6,491,998 B1 * | 12/2002 | Heitz | A47L 13/20 15/208 |
| 6,720,058 B1 | 4/2004 | Weeks et al. | |
| 6,957,958 B2 | 10/2005 | Rowe | |
| 7,303,804 B2 | 12/2007 | Yoshida | |
| 7,540,680 B2 | 6/2009 | Feldman et al. | |
| 8,152,929 B1 | 4/2012 | Perring | |
| 8,308,702 B2 | 11/2012 | Batchvarova et al. | |
| 9,080,267 B2 | 7/2015 | Batchvarova et al. | |
| 9,609,983 B2 | 4/2017 | McCarthy | |
| 9,713,553 B2 * | 7/2017 | Engl | A61F 13/00 |
| 2002/0090591 A1 | 7/2002 | Fischer | |
| 2002/0122832 A1 | 9/2002 | Hanke et al. | |
| 2003/0176827 A1 | 9/2003 | Chandra et al. | |
| 2003/0217425 A1 * | 11/2003 | Datta | A47L 13/18 15/227 |
| 2004/0228990 A1 | 11/2004 | Hines | |
| 2004/0265534 A1 | 12/2004 | Curro | |
| 2004/0267245 A1 * | 12/2004 | Riney | A61B 46/23 606/1 |
| 2005/0031828 A1 * | 2/2005 | Yoshida | A47L 13/20 428/92 |
| 2005/0202068 A1 * | 9/2005 | Hasenoehrl | A47K 7/03 424/443 |
| 2006/0039742 A1 | 2/2006 | Cable | |
| 2006/0075589 A1 | 4/2006 | Choi | |
| 2006/0236478 A1 * | 10/2006 | Hohlbein | A46B 9/028 15/110 |
| 2008/0125687 A1 | 5/2008 | Flick et al. | |
| 2008/0177253 A1 | 7/2008 | Boehringer et al. | |
| 2008/0299858 A1 * | 12/2008 | Salmon | D04H 1/498 442/381 |
| 2009/0103969 A1 * | 4/2009 | Feldman | A46B 11/0003 401/183 |
| 2009/0131960 A1 * | 5/2009 | Tanaka | A61B 17/244 606/161 |
| 2009/0226506 A1 | 9/2009 | Masters et al. | |
| 2010/0146724 A1 | 6/2010 | Jo | |
| 2010/0228267 A1 | 9/2010 | Mercado | |
| 2011/0046607 A1 | 2/2011 | Halevy | |
| 2011/0193400 A1 | 8/2011 | Kwon et al. | |
| 2012/0046670 A1 | 2/2012 | Engl | |
| 2015/0305945 A1 | 10/2015 | Engl et al. | |
| 2015/0366413 A1 | 12/2015 | Dudzic et al. | |
| 2016/0066763 A1 | 3/2016 | Xu | |
| 2016/0183757 A1 | 6/2016 | Xu | |
| 2016/0262590 A1 | 9/2016 | Link et al. | |
| 2016/0270970 A2 | 9/2016 | Engl et al. | |

FOREIGN PATENT DOCUMENTS

| | | |
|---|---|---|
| DE | 19839505 | 3/2000 |
| EP | 0552933 | 7/1993 |
| EP | 0632990 | 7/1994 |
| EP | 0874073 | 4/1998 |
| JP | 02239829 | 9/1990 |
| RU | 2153838 | 8/2000 |
| RU | 2181024 | 4/2002 |
| WO | WO 1998/46818 | 10/1998 |
| WO | WO 1998/57570 | 12/1998 |
| WO | WO 2007/015729 | 2/2007 |
| WO | WO 2007/105883 | 9/2007 |
| WO | WO 2016/038287 | 3/2016 |
| WO | WO 2016/038289 | 3/2016 |

OTHER PUBLICATIONS

Hansaplast Wundreinigungstuch, www.hansaplast.de (accessed Jan. 2007).

Easyderm®, "Easyderm" Total Body Cleansing System, Apr. 2006.

Enjo®, "Enjo for your Home", Catalogue Version 2.1 (Admitted Prior Art—Undated), (Prior to Jan. 1, 2008).

Interlocutory Decision in Opposition Proceedings dated Mar. 29, 2016, issued in related European Patent Application 10704304.4 (18 pgs. for each document).

* cited by examiner

WOUND CLEANING ASSEMBLY

CROSS-REFERENCE TO RELATED APPLICATIONS

This application claims priority to and is a Continuation of U.S. patent application Ser. No. 15/649,844, filed on Jul. 14, 2017, which is a Continuation of U.S. patent application Ser. No. 14/790,398, filed on Jul. 2, 2015 (now issued U.S. Pat. No. 9,713,553), which is a Continuation of U.S. patent application Ser. No. 13/146,729, with a 371(c) filing date of Oct. 4, 2011, which application was abandoned and was a 371 national application filed from International Application No. PCT/AT2010/000027, filed Jan. 26, 2010; and Austrian Patent Application No. A 145/2009 filed Jan. 28, 2009, each of which is incorporated herein by reference in its entirety.

STATEMENT REGARDING FEDERALLY SPONSORED RESEARCH OR DEVELOPMENT

Not applicable.

BACKGROUND OF THE INVENTION

The present invention relates to a wound cleansing assembly, used for cleansing wounds, an arrangement comprising a wound cleansing assembly and a packaging, as well as a method for producing such a wound cleansing assembly.

The start of any medical wound treatment is the successful cleansing of the wound. For this purpose, various methods and means have been used in prior art. The cleansing of wounds via cotton pads is largely known and used. Also known are surgical or hydro-surgical cleansing methods or the application of impulse wave therapy or ultrasound. The central requirements for a successful wound cleansing are that on the one hand any contaminants are removed as completely as possible and on the other hand any already beginning healing processes are not reversed by destroying and/or rubbing off any already newly forming intact wound closures. This particularly applies for drawn-out medical treatments of chronic wounds.

The so-called debridement is particularly important for the treatment of acute wounds and in particular for chronic wounds. This represents the process of wound base preparation, in which substances formed by the body itself or in other words human material is removed, such as excess fluids, fibrin coatings, dead tissue of the epidermis, e.g., excess keratin material or dead keratinocytes and/or coatings of dead tissue (necroses). Presently, such debridement can practically be achieved only via technical medical means, such as hydro-surgery, impulse wave therapy, or by surgery. Further, in prior art the extended application of specially moistened wound bandages is contested, which after an extended period of application shall achieve such a debridement effect. The methods known in prior art are expensive and painful and partially aggressive. During the removal of the biological material disturbing the healing process of the wound the purpose of debridement is to preserve the newly sprouting skin spots, i.e. the granulation tissue, uncompromised to the extent possible until the early formation of epithelial cells and only to remove the disturbing substances. In the methods of prior art this goal is not achieved to the extent desired.

Overall, the methods and means used in prior art are partially very expensive and only insufficiently fulfill the above-mentioned central requirements.

BRIEF SUMMARY OF THE INVENTION

Therefore, the objective of the present invention is to provide a way for wound cleansing and particularly for debridement in which a careful but simply performed process for wound cleansing, particularly debridement is possible, which satisfactorily removes the contaminants but does not compromise the already beginning healing process or even reverses it.

This is achieved according to the invention in that the wound cleansing assembly comprises or is a wound cleansing cloth, which comprises at least one carrier layer and threads are arranged on the carrier layer and project from said carrier layer, made, preferably exclusively, from synthetic fibers, preferably plastic fibers.

It has shown that using such wound cleansing cloths with threads made from synthetic fibers wounds can be cleansed in a very simple manner, yet highly efficiently and without and/or with only minimal disturbance of the wound healing processes that have already occurred. Here, the synthetic fibers exhibit several advantages. On the one hand, they can easily and reliably be sterilized. On the other hand, by the electro-static attraction they bind the contaminants to be removed from the wound. The dirt particles removed from the wound are reliably held between the threads of the wound cleansing cloth and are not released back into the wound.

Here, the term wound cleansing includes both the removal of external bodies and/or particles, thus substances not formed by the body itself, but also the debridement, thus the process of preparing the wound base, in which substances and/or human material formed by the body itself are removed from the skin and/or from the wound, such as excess fluids, fibrin coatings, dead tissue of the epidermis, such as excess keratin material or dead keratinocytes and/or coatings of dead tissue (necroses). The wound cleansing assemblies according to the invention are particularly well suited for the debridement and here particularly for the treatment of acute as well as chronic wounds, because when using it any biological material disturbing the wound healing process is removed from the wound in a particularly careful but also effective manner and simultaneously the newly sprouting skin spots in the form of granulation tissue remains preserved. Here, debridement also relates to one of the most important measures of managing acute as well as chronic wounds because without the debridement healing cannot occur according to the known medical processes leading to the wound healing. In particular for debridement the wound cleansing assembly according to the invention is characterized such that the above-mentioned disturbing biological material and/or human material is effectively removed from the wound by using the wound cleansing cloth and subsequently it is held between the threads of the wound cleansing cloth and thus cannot return back into the wound or be released to the skin. In other words, the wound cleansing assembly according to the invention is characterized such that it can actively pick up the material to be removed during debridement into the area between the threads projecting from the carrier layer and then hold it there so that any already removed biological material cannot accidentally return into the wound. The wound cleansing cloth may be used in a dry as well as in a moistened form and/or prior to application it may be soaked in liquids generally known and/or used in medicine. The wound cleansing cloth preferably represents a sterilized product and/or a medical product which fulfills the requirements of applicable standards and legal requirements for medical products.

Generally speaking, using the wound cleansing assemblies according to the invention a method for cleansing, particularly debridement of a wound and/or the skin can be performed. Here, external contaminants and/or disturbing biological material and/or human material produced by the body itself can be removed from the wound and/or from the skin. For this purpose, the wound must only be wiped and/or cleansed with the fibers projecting from the carrier layer. However, as already mentioned, the wound cleansing assemblies according to the invention are particularly well suited for debridement, thus a method in which biological material and/or human material produced by the body itself are removed from the wound and/or from the skin. In other words, using the wound cleansing assembly according to the invention a method can be performed for picking up human material off the skin and/or out of a wound. In particular for debridement, the wound cleansing assemblies according to the invention can be used for the indications named in the following: for example it can fight an ongoing settlement of bacteria in the wound in the form of a liquid bio-film, which leads to the colonization or local infection of the wound. Thus, wound cleansing assemblies according to the invention can be used in a particularly well suited fashion to remove colonies of bacteria in a bio-film from the wound, which lead to systematic infections of the patient. Furthermore, dry fibrin coatings can be removed, which otherwise lead to a blockage of the wound healing process by blocking the wound base and/or wound edge necessary for healing. The same applies for the reduction of plate-like necroses in the form of dead tissue in moist as well as in dry forms. Furthermore, wounds and wound edges with excess keratin production (hyper-keratoses) and dead keratin and/or tissue cells can be treated effectively and carefully.

The threads may be embodied relatively soft, however they may also be relatively stiff like bristles. Theoretically, the threads may also show components of non-synthetic fibers. However preferably it is provided that they are made exclusively from synthetic fibers. Overall, the wound cleansing cloth forms a textile fabric, which can be used, if applicable after being moistened, quickly and simply for a particular medical wound cleansing and/or debridement, particularly for acute or chronic wounds. The term synthetic fiber is understood initially to include all non-natural fibers in general, particularly plastic fibers.

Particularly preferred it is provided that at least some, preferably at least 50% of the threads exhibit ends preferably cut-off and freely projecting from the side facing away from the carrier layer. Beneficially at least 80% to 90%, and preferably all threads exhibit freely projecting, preferably cut-off ends at the side facing away from the carrier layer. Due to these freely projecting ends the threads develop a type of razorblade effect, which renders the removal of contaminants and/or disturbing biological material from the wound particularly effective, especially material produced by the body itself. In this sense it is beneficially even provided that the threads exhibit ends and/or end surfaces extending, particularly cut at an angle in reference to their longitudinal extension. Here, "at an angle" is understood as all angles extending neither orthogonally and/or normally nor parallel in reference to the longitudinal extension of the threads. The longitudinal extension of the threads is here understood as their alignment in the extended state. Preferably the ends and/or end surfaces extending at an angle in reference to their longitudinal extension form an angle ranging from 70° to 80° with the longitudinal extension of the thread. This shall not be understood such that the threads must always be extended. Although the threads may be embodied with different hardness and/or bristle-like, they always show a certain beneficial flexibility, though. In order to allow achieving the desired wound cleansing effect as quickly as possible and over a certain area particular embodiments provide that the threads form a pile arranged at the carrier layer and projecting therefrom.

It is also advantageous for the carrier layer, preferably the entire wound cleansing cloth to comprise synthetic fibers, preferably plastic fibers or even better to consist of such fibers. Wound cleansing cloths of this type can be easily produced. For example, a method for the production of a wound cleansing cloth may provide that two carrier layers are jointly produced in a first processing step in the form of stitched fabric, preferably knitted or woven, with in this first processing step an intermediate layer being formed between the two carrier layers from threads extending between the two carrier layers, and incorporated in the two carrier layers and the threads being separated, preferably cut in a second processing step, preferably in the middle between the two carrier layers. In such a production manner it is simultaneously achieved that the threads exhibit ends and/or end surfaces extending, preferably cut at an angle in reference to their longitudinal extension. Alternative production methods provide that a wound cleansing cloth is produced preferably by weaving or knitting, comprising a carrier layer and threads made from synthetic fibers projecting from said carrier layer and subsequently the projecting fibers are cut preferably at an angle in reference to their longitudinal extension. This way, the threads may be cut both to the desired length as well as at a desired angle. Suitable cutting devices are known in prior art. The synthetic fibers and/or the carrier layer, preferably the entire wound cleansing cloth, preferably consist of materials, such as polyester, polyamide, and/or polyacrylics. These different plastics can be used as pure substances for the entire wound cleansing cloth. However, it is also possible to produce the threads and/or the carrier layer and/or the entire wound cleansing cloth from mixtures of synthetic fibers comprising polyester and/or polyamide and/or polyacrylics. For example, it is possible to use synthetic fibers comprising 80% polyacrylics and 20% polyester for the threads. The carrier layer may be made from 100% polyester, e.g. However, preferred embodiments also provide making the threads from 100% polyester.

It will frequently occur that the wound cleansing cloth according to the invention is used as a single-use item and discarded after use. In the sense of simply discarding it, is beneficial for the entire wound cleansing cloth to be embodied as homogeneously as possible. In this sense it is preferably provided for the threads and/or the carrier layer, preferably the entire wound cleansing cloth to comprise at least 90% by weight, preferably entirely a single synthetic material and/or plastic, preferably polyester or polyamide or polyacrylics. In all embodiments the threads and/or the carrier layer may be coated with a coating mass, preferably 100% polyacrylics. The coating mass may be brushed onto the fibers in a liquid form using a cylinder and be calendared. It is beneficial to use an amount ranging from 50 to 70 gram coating mass per square meter, preferred are here 60 g/m$^2$.

Within the scope of the invention it may also be provided that at least some of the threads projecting from the carrier layer and/or at least some of the threads forming the carrier layer are preferably pure silver threads and/or preferably pure copper threads and/or comprise synthetic fibers with a silver coating and/or copper coating or are made therefrom.

By the use of silver and/or copper a temporary or permanent anti-bacterial effect can be achieved. It may relate to pure silver and/or copper threads, i.e. threads which comprise exclusively silver or copper to the level of purity achievable during the production process, or threads containing silver or copper. The coating of synthetic fibers with silver and/or copper may be achieved by immersing the fibers or the finished produced wound cleansing cloths in silver and/or copper baths or by an appropriate spraying or vapor coating. In all these cases the threads may be incorporated in the carrier layer and/or in the pile formed by the threads.

In order to achieve the desired temporary or even permanent anti-bacterial effect it may also be provided that nanoparticles adhere to and/or are arranged at the synthetic fibers of the carrier layer and/or the synthetic fibers of the threads projecting from the carrier layer. For this purpose, the fibers or the wound cleansing cloth and/or the wound cleansing assembly may be immersed in baths with the respective nanoparticles or be sprayed or vapor coated with nanoparticles. The nanoparticles are accepted by the fiber core, which leads to the desired antibacterial effect. Using the nanoparticles, other additional features may be achieved, too, such as disinfection.

The use of preferably exclusively synthetic fibers, preferably plastic fibers, is also advantageous in that provably such fibers trigger no allergic reactions.

As already explained, the invention therefore particularly relates to a cloth for the use and/or for the specific application as a wound cleansing assembly and/or as a wound cleansing cloth. Therefore, the invention also relates to a cloth for cleansing, particularly for the debridement of wounds or skin, which comprises a carrier layer and threads arranged at the carrier layer and projecting from said carrier layer, preferably comprising exclusively synthetic fibers, preferably plastic fibers.

The preferred embodiments of this cloth and/or this wound cleansing cloth and/or the wound cleansing assembly have already been partially explained and will be once more explained in greater detail using the exemplary embodiment shown in the figures. Here, it must be mentioned that the invention therefore also relates to the use of synthetic fibers for the production of a wound cleansing assembly or a wound cleansing cloth of a wound cleansing assembly with the above-mentioned features for cleansing and/or for the debridement of wounds or the skin. In the above-mentioned applications and/or specific uses the medical use by a physician is focused on, particularly, the surgical or therapeutic treatment of acute or chronic wounds.

In order to allow providing a sterile wound cleansing cloth and/or cloth for cleansing wounds and/or for debridement, the invention further provides an arrangement which comprises at least one wound cleansing cloth or at least one respective cloth and a preferably air-tight, sealed package, preferably a plastic package, with at least one wound cleansing cloth or cloth being packaged in a sterile fashion.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

Additional features and details of different embodiment variants of the present invention are discernible from the following description of the figures. They show.

DETAILED DESCRIPTION OF PREFERRED EMBODIMENT

Figure 1:
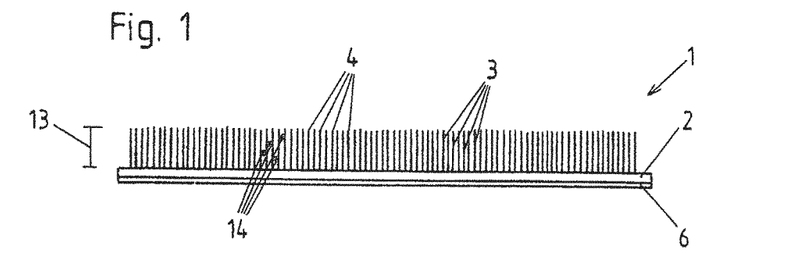
FIG. 1 a schematic side view of a wound cleansing cloth according to the invention.

As discernible in a side view according to FIG. 1, the threads 3 are fastened at a carrier layer 2. They project laterally from the carrier layer 2 and are beneficially arranged so tightly next to each other that they form a type of pile. Even if the threads are shown extending linearly in the schematic illustration shown, it is ultimately a matter of their stiffness and/or elasticity to what extent the threads 3 actually project like bristles from the carrier layer 2, as shown here. Even in the unstressed state, shown here, it is not mandatory for all fibers 3 to project linearly from the carrier layer 2 in the longitudinal direction. In any case, their elasticity shall be embodied such that they bend appropriately, as soon as the wound cleansing cloth is pressed against the wound. The hardness and/or pliability of the threads may be adjusted as desired by their thickness and the material used. Preferably used threads 3 comprise from 0.5 to 20 D-Tex (1 D-Tex=1 g/10000 m). Particularly preferred embodiments provide that the threads are 6.7 D-Tex. The height of the pile 13 and/or the length of the threads 3 beneficially ranges from 3 mm to 30 mm, preferably from 3 to 12 mm, particularly preferred is a pile 13 having a height of 8 mm. Beneficially, fibers with a mass per area unit ranging from 500 to 900 g/m2 (gram per square meter) and/or particularly preferred of approx. 700 g/m2 are used for the carrier layer 2 and/or the threads 3. The carrier layer 2 is beneficially embodied in the form of a stitched web. It may also represent to a web or a knitted fabric, for example. The threads 3 projecting from the carrier layer 2 are beneficially interwoven and/or knitted into the carrier layer 2. It is particularly preferred that the woven fabric is a woven web. Here, the fibers and/or the threads 3 particularly well adhere to the carrier layer 2, so that they cannot accidentally separate from the carrier layer 2 during the process of wound cleansing and/or debridement. Furthermore, no lint develops in webs, i.e. no separation of individual fibers from the threads 3 occurs. In particular, the webs may be embodied with or without any reinforcement layer 6, due to their high inert stiffness. Any potentially present silver and/or copper threads may be also interwoven. Beneficially the carrier layer 2 comprises 7 to 12, preferably 9 stitches/cm2 and 10 to 14, preferably 12 rows/cm2. In order to stabilize the carrier layer 2 embodied as a stitched fabric, in preferred embodiments, such as the one shown in FIG. 1, the carrier layer 2 may be coated with a reinforcement layer, preferably at the side facing away from the projecting threads 3, connecting the stitches of the carrier layer 2 preferably continuously. The reinforcement layer 6 may not only be used in carrier layers 2 embodied as webs. Rather it may be provided in general that in and/or at the carrier layer 2, preferably at the side of the carrier layer 2 facing away from the projecting threads 3, at least one reinforcement layer 6 is arranged. One or more reinforcement layers 6 may be provided on the carrier layer 2. In any case, by the reinforcement layer and/or layers 6 it is achieved that on the one hand, the threads 3 are held particularly tightly at the carrier layer 2. On the other hand, the stiffness of the carrier layer 2 is also increased which during the treatment of the wound or the skin leads to the pressure applied onto the wound cleansing cloth being evenly distributed over an area of the wound. The reinforcement layer(s) 6 is (are) generally embodied as additional layer(s), fastened at the carrier layer by suitable measures.

This type of reinforcement via at least one reinforcement layer 6 can be achieved by different means. For example, the reinforcement layer 6 may be applied in the form of a curing adhesive layer on the back of the carrier layer 2 facing away from the threads 3. However, the reinforcement layer 6 may also represent a coating of synthetic materials which become liquid under heat and which cure when cooling. Here, e.g., polyester may be used as the material. The mass per area unit of such coatings beneficially range from 40 g to 120 g per m2. Alternatively, a reinforcement layer 6 may also be produced as a membrane made from synthetic materials. Here, too, preferably polyester materials may be used. The membranes represent thin skins and/or elastic films. In particular, they may serve as separating layers. The membranes may also be impermeable with regards to moisture and/or liquids or partially permeable or even entirely permeable. The membranes may be applied by way of punctual lamination on the carrier layer 2 e.g., as elastic films using particular adhesives. Alternatively, it is also possible for the membrane to be applied on the carrier layer 2 by spray lamination using an adhesive in the form of an elastic film. Useful masses per area unit for such membranes range from 10 g to 60 g per m2. Alternatively, the reinforcement layer 6 may also be embodied in the form of a rubber coating using synthetic materials, such as polyester materials or natural substances, such as rubber. The lamination can occur with all common systems. The mass per area unit of such reinforcement layers 6 in the form of rubber coatings shall beneficially range from 20 to 60 g per m2. Another variant of a reinforcement layer 6 provides for it comprising a foam made from a synthetic material, such as polyester. The mass pre area unit preferably ranges from 10 to 60 g per m2. The fastening to a carrier layer 2 can once more occur via lamination. The thickness of such reinforcement layers 6 comprising foam may amount e.g., from 5 to 20 mm. In particular when foam is provided as a reinforcement layer 6 additional reinforcement layers 6, such as membranes or rubber coatings may be provided at the carrier layer 2 in order to achieve permeability with regards to moisture and/or liquids.

Mentioning another example, one of the reinforcement layer or layers 6 may also be embodied as a knitted and/or woven fibrous fabric comprising a synthetic material. For example, this fibrous fabric may be adhered to the carrier layer 2. The fabric may be provided with nubs, similar to any other reinforcement layer 6 or the carrier layer 2 itself, e.g., made from rubber, in order to ensure better fastening.

In general it must be pointed out that depending on the desired characteristics one or several reinforcement layers 6 may be arranged at the carrier layer 2. The reinforcement layers 6 may be embodied repelling or impermeable to liquids or moisture so that the person performing the treatment does not come into contact with the substances removed from the wounds and/or the skin. Another important effect, which can be achieved by the reinforcement layer(s) 6, is the stiffening of the wound cleansing cloth (1) and/or the wound cleansing assembly.

Figure 2:
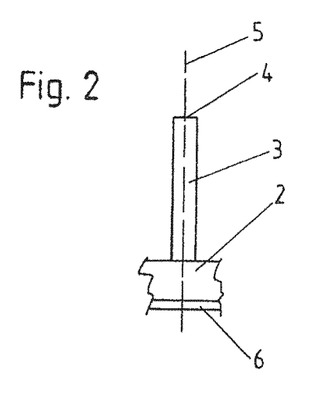
FIGS. 2 and 3 detailed views thereof.
Figure 3:
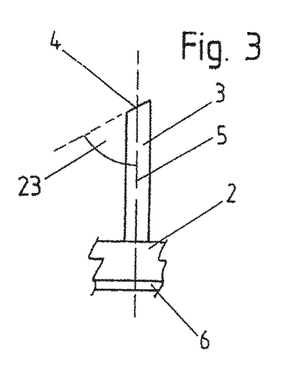

FIG. 2 shows in detail an embodiment in which the freely projecting ends 4 of the threads 3 are arranged orthogonally and/or normally in reference to the longitudinal extension 5 of the threads 3 arranged extended. A particularly good cleaning effect is achieved by these freely projecting ends 4. FIG. 3 shows a particularly preferred embodiment, in which the freely projecting ends 4 and/or their end surfaces are not extending orthogonally, but at an angle in reference to the longitudinal extension of the threads 3. The angle results in a defined cutting edge at an intersection of the end surface and a sidewall of the thread. This creates a particularly good razor-blade like effect, which removes the contaminants and/or the biological material from the wound in a particularly effective fashion. The angle 23 between the freely projecting ends 4 and/or their end surfaces and the longitudinal extension 5 of the threads 3 beneficially ranges from 70° to 80°. In the embodiments shown in FIG. 2 and FIG. 3, the threads are single-fiber threads. Returning to FIG. 1, reference is made once more to another positive feature of the use of synthetic fibers for the threads 3. As indicated schematically, any contaminants 14 and/or the biological material, once removed from the wound, remain trapped in the pile on the one hand by the density of the pile formed by the threads 3, and on the other hand also by the electrostatic attraction of the synthetic fibers of the threads 3, so that there is no risk for them returning into the wound during further use of the wound cleansing cloth 1.

In preferred embodiments of the invention it may be provided that synthetic fibers of the carrier layer 2 and/or the synthetic fibers of the threads 3 projecting from the carrier layer 2 are shrunk by heat-treating, preferably via thermal treatment. The heating can occur e.g., at 100-200°. The fibers and thus the treads 3 become more stable and perhaps more colorfast by the heating process. The increased stability of the threads 3 improves the effectiveness of the wound cleansing assembly. The heating may be performed on the crude fiber prior to producing the wound cleansing cloth 1 but also on an otherwise already completely finished wound cleansing cloth 1. Shrinkage may occur by the heating process, which may range e.g., from 10 to 20% in reference to the previous length of the threads 3 and/or the fibers.

Figure 4:
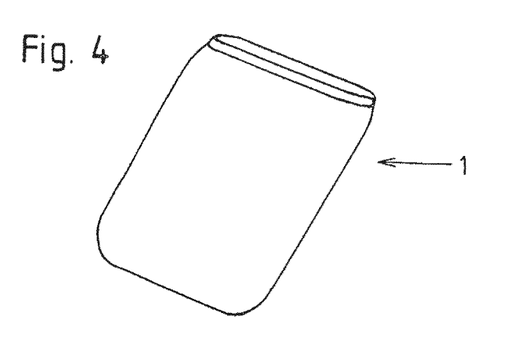
FIG. 4 an exemplary embodiment according to the invention in the form of a glove-like wound cleansing cloth.

FIG. 4 shows a glove-like formed exemplary embodiment of a wound cleansing cloth according to the invention. It may be produced, e.g., by a respective sewing together two wound cleansing cloths shown in FIG. 1, with the threads 3 pointing outwardly.

Figure 5:
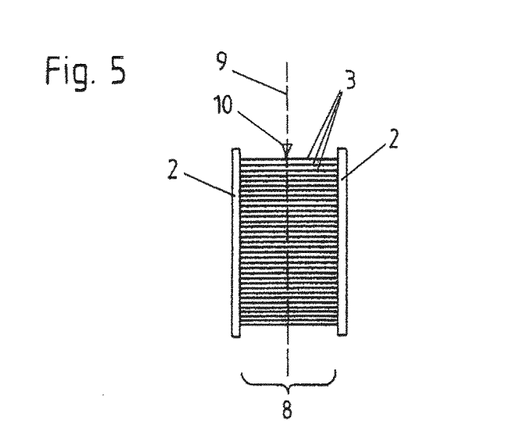
FIG. 5 a schematic sketch that explains a particular production process.

FIG. 5 shows a schematic drawing, based on which a preferred production method is explained for wound cleansing cloths 1 and/or fabrics according to the invention. This method provides that two carrier layers 2 are produced together in the form of stitched fabrics in a first processing step, with in this first processing step an intermediate layer 8 made from threads extending between the two carrier layers and incorporated into the two carrier layers 2 being embodied between the two carrier layers 2. Here, knitting or weaving techniques known per se may be used, for example. The threads 3 are beneficially knitted and/or woven in as early as during the knitting and/or weaving of the carrier layers 2. Such knitting and/or weaving techniques are known in prior art and it is not necessary to explain them. When this type of stitched fabric is finished, as shown schematically in FIG. 5, the threads 3 are preferably severed in a second processing step, preferably in the middle between the two carrier layer 2, preferably cut. FIG. 5 schematically shows the separating tool and/or knife 10 and the separating line 9. When a certain pressure is applied upon the separation tool and/or knife 10 for cutting and/or severing the threads 3 here automatically the preferred freely projecting ends 4 of the threads 3 are produced, shown schematically in FIG. 3 and arranged at an angle in reference to the longitudinal extension 5 of the threads 3.

Subsequent to the already described processing steps, if desired, the already described reinforcement layer 6 may be applied on the rear sides of the carrier layers 2 facing away from the threads 3. Furthermore, it is also possible to brush and/or roll the coating mass mentioned at the outset, preferably comprising 100% polyacrylic, onto the fibers, primarily the threads 3 in a liquid form.

Alternatively, a production process may also be provided, in which a wound cleansing cloth 1 is prepared separately, preferably by way of weaving or knitting, having a carrier layer 2 and threads 3 comprising synthetic fibers projecting from said carrier layer 2, and subsequently the projecting threads 3 are cut preferably at an angle in reference to their longitudinal extension 5. FIG. 1 shows such a wound cleansing cloth 1 after the cutting of the threads 3. The threads may be cut both in the desired length as well as the desired angle. Suitable cutting devices are known in prior art. One or more reinforcement layers 6 optionally provided can be fastened prior or after the cutting of the threads 3.

Figure 6:
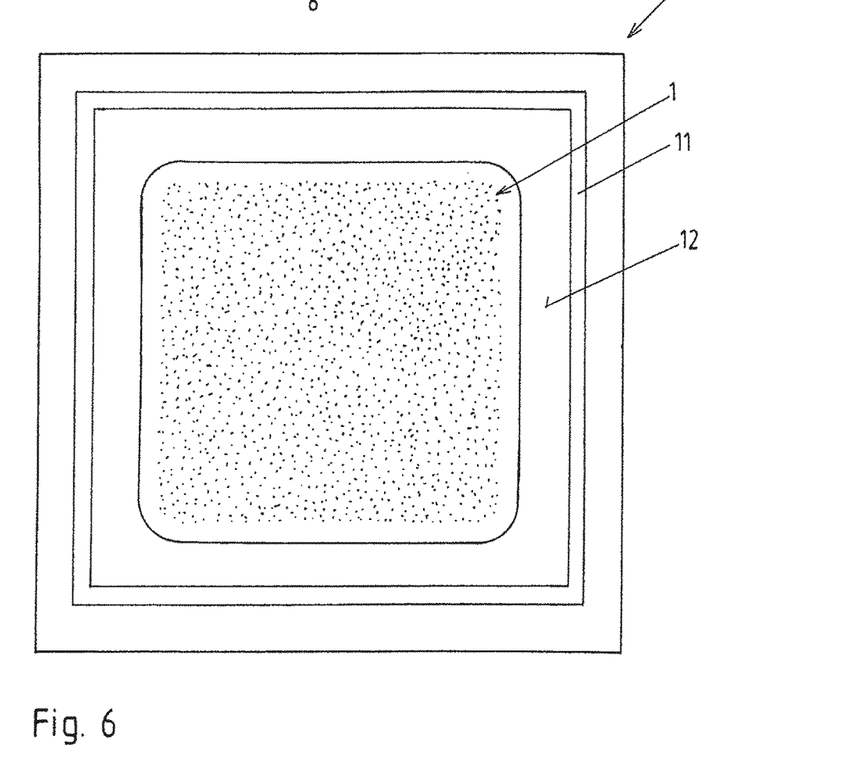
FIG. 6 an arrangement according to the invention with a wound cleansing cloth enclosed in a package in a sterile fashion.

Furthermore, FIG. 6 shows an arrangement according to the invention comprising a package 7 and a wound cleansing cloth 1 according to the invention of the type described. The wound cleansing cloth 1 is packaged in a sterile fashion in the package 7. The package 7 may be embodied, e.g., as a plastic package and/or film package. As indicated in FIG. 6, it may represent e.g., a two-layered structure. This may comprise a cover film 12 and a sterilizing paper arranged at the other side, with the cover film 12 and the sterilizing paper welded to each other via a circumferentially closed welding seam 11. However, the use of other sterile packaging known in prior art is possible. The wound cleansing cloth 1 can be sterilized prior to packaging by known sterilizing methods, such as steam sterilization, gamma-ray sterilization, or oxygen sterilization. The length of the edges of the wound cleansing cloth 1 and/or the packaging beneficially range from 5 to 20 cm, preferably from 10 to 20 cm.

Figure 7:
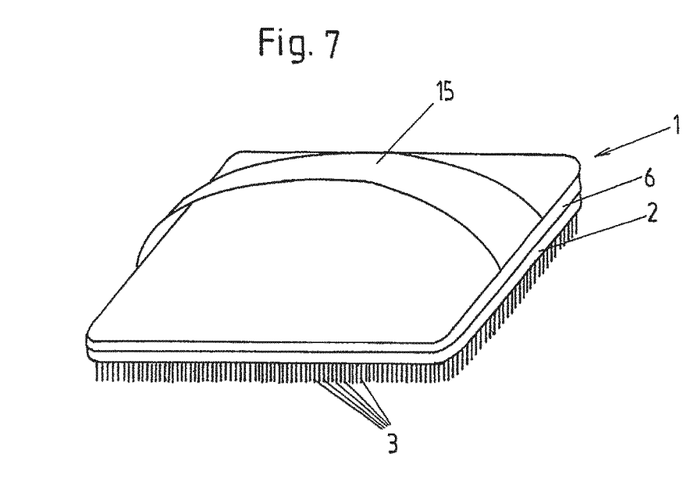
FIG. 7 a wound cleansing assembly according to the invention with a reinforcement layer and a loop for better handling.
Figure 8:
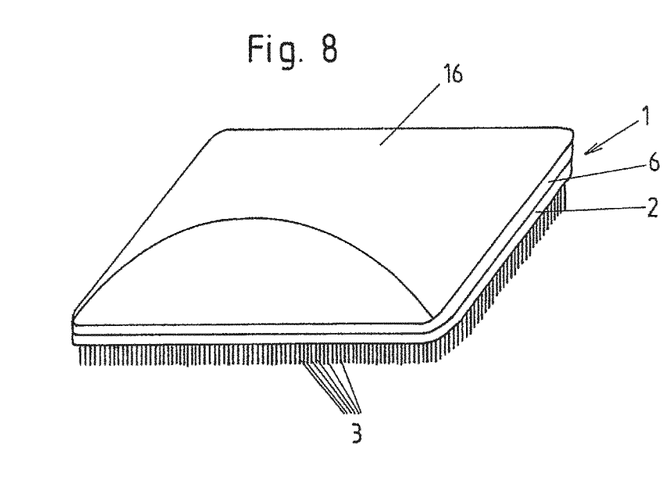
FIG. 8 another exemplary embodiment of a wound cleansing assembly according to the invention provided with a reinforcement layer and a pocket for grasping.

FIG. 7 shows another exemplary embodiment of a wound cleansing assembly according to the invention. A reinforcement layer 6 is applied on the carrier layer 2 on the side facing away from the threads 3. When selecting appropriate materials and thicknesses it may ensure on the one hand an increased stiffness of the wound cleansing cloth. On the other hand, when embodied in a moisture and/or liquid-impermeable fashion, the reinforcement layer 6 may protect the hand of the person performing the wound treatment from coming into contact with the materials removed from the wound. In order to simplify handling, in the exemplary embodiment according to FIG. 7, a loop 15 is provided at the rear of the carrier layer 2 and/or the side facing away from the threads 3. The person performing the treatment can engage this loop 15 with the hand so that the wound cleansing assembly can be held securely and tightly during the wiping and/or cleansing of the wound using the threads 3. The loop 15 may comprise elastic or non-elastic materials. The same applies to the exemplary embodiment according to FIG. 8, in which instead of the loop 15, a pocket 16 is provided which the person performing the treatment can engage by his/her hand. Similar to all other exemplary embodiments, the side of the wound cleansing cloth 1 at the side facing away from the threads 3, which is grasped by the person performing the treatment, may be provided with nubs. This increases slip-resistance.

Figure 9:
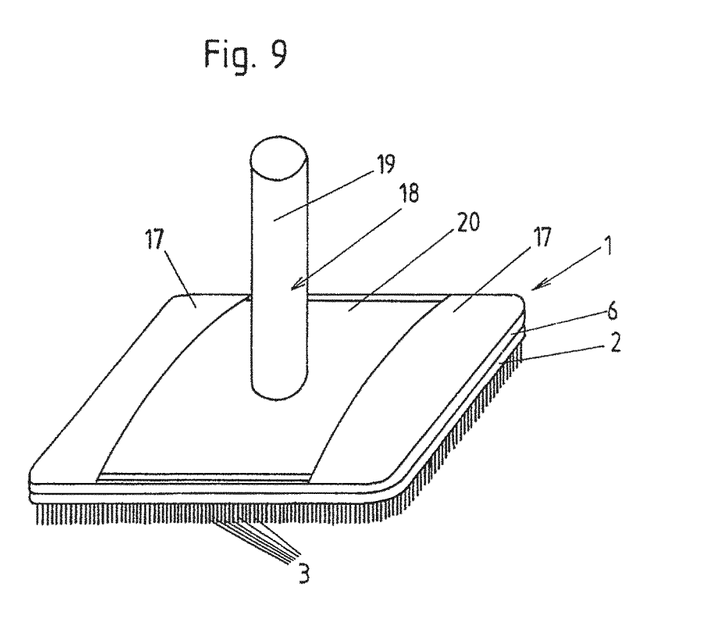
FIG. 9 another exemplary embodiment according to the invention, in which the wound cleansing cloth is fastened at a carrying body, and FIG. 10 another wound cleansing assembly according to the invention, in which the wound cleansing cloth is also fastened to a carrying body.
Figure 10:
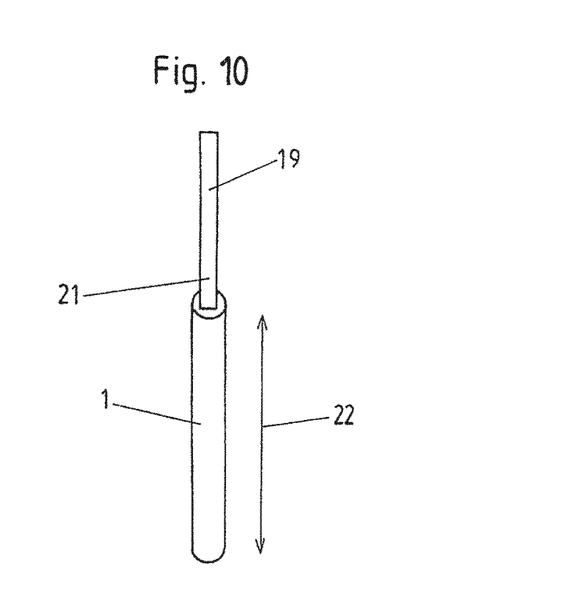

In other embodiments according to the invention, shown e.g., in FIGS. 9 and 10, it may also be provided that the wound cleansing cloth 1 is arranged and/or fastened to a preferably stiff carrier body, preferably in an interchangeable fashion. The use of such carrier bodies 18 is particularly recommended when the wound cleansing cloth 1 is to be used for the treatment of smaller or deeper wounds with smaller exterior dimensions. For example, it may be provided that the wound cleansing cloth 1 has edge lengths from 3 cm to 6 cm, preferably 5 cm. In the exemplary embodiment shown, the carrying body 18 is formed by a plate 20 and a handle 19 arranged thereat. Both of them as well as the entire carrying body 18 are beneficially embodied in an essentially stiff fashion. In the variant shown, the fastening of the carrying body 18 and/or a plate 20 occurs by inserting the plate 20 into the insertion pockets and/or tapes 17 at the edge of the wound cleansing cloth 1. Of course, other fastening variants, such as Velcro, are also possible and can be used, at which perhaps additional objects are fastened.

FIG. 10 shows a variant of a wound cleansing assembly according to the invention, in which the wound cleansing cloth 1 is fastened at a rod. The rod 21 in turn shows a handle 19, at which the wound cleansing assembly may be grasped. The threads 3 of the wound cleansing cloth 1 projecting outwardly are not shown separately in FIG. 10. In the variants according to FIGS. 9 and 10 as well as in other such embodiments the wound cleansing cloth 1 can be fastened at the carrying body 18 in a detachable or fixed manner. Embodiments according to the invention with preferably essentially stiff carrying bodies 18 are particularly well suited if they can apply pressure upon the desired site and/or wound to be treated in a targeted fashion. The variant according to FIG. 10 is particularly recommended to treat small and hard to access areas of a wound or of such skin areas. The rod 21 is beneficially extended inside the wound cleansing cloth 1 in order to stiffen it appropriately. For this purpose, the wound cleansing cloth 1 can be wound, e.g., around the rod 21 and/or form a respective pocket into which the rod 21 is inserted.

The multitude of embodiments according to the invention shown shall indicate that the invention is not limited to the variants concretely shown. Rather it is possible to combine the above-mentioned preferred embodiments and features in order to provide additional wound cleansing assemblies according to the invention particularly beneficial for the respective use.

LEGEND OF THE REFERENCE CHARACTERS

1 Wound cleansing cloth
2 Carrier layer
3 Threads
4 End
5 Longitudinal extension
6 Reinforcement layer
7 Packaging 8 Intermediate layer
9 Separating line
10 Separating tool
11 Welding seam
12 Cover film
13 Height of pile
14 Contaminant
15 Loop
16 Pocket
17 Insertion pocket or insertion tape
18 Carrying body
19 Handle
20 Plate
21 Rod
22 Length
23 Angle From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A wound cleaning assembly which comprises a wound cleansing cloth (1) having at least one supporting layer (2) and single-fiber threads (3) arranged on the supporting layer (2) and protruding from the supporting layer (2), at least some of the single-fiber threads comprising a synthetic fiber, wherein at least some of the single-fiber threads (3) have protruding ends (4) on the side thereof facing away from the supporting layer (2), at least some of the single-fiber threads further comprising end surfaces (4) which extend at an angle (23) neither orthogonal nor parallel with reference to the longitudinal axis (5) thereof, wherein the length of the single-fiber threads range from 3 mm to 30 mm, and wherein the single-fiber threads have a dtex value of between about 0.5 and 20, and wherein the wound cleansing cloth is packed in a sterile manner in a sealed packaging.

2. The wound cleaning assembly of claim 1, wherein the synthetic fiber comprises a polyester fiber.

3. The wound cleaning assembly of claim 1, wherein the angle is an acute angle with reference to the longitudinal axis thereof.

4. The wound cleaning assembly of claim 3, wherein the acute angle is from 70 to 80 degrees.

5. The wound cleaning assembly of claim 3, wherein the end surfaces of the single-fiber threads are unitary and non-curved.

6. The wound cleaning assembly of claim 3, wherein the angle is formed by cutting the single-fiber threads.

7. The wound cleaning assembly of claim 3, wherein the angle forms a defined cutting edge at an intersection of the end surface and a sidewall of the single-fiber thread.

8. The wound cleaning assembly of claim 1, wherein the end surfaces of the single-fiber threads are unitary and non-curved.

9. The wound cleaning assembly of claim 1, wherein the angle is formed by cutting the single-fiber threads.

10. The wound cleaning assembly of claim 9, wherein the angle forms a defined cutting edge at an intersection of the end surface and a sidewall of the single-fiber thread.

11. The wound cleaning assembly of claim 1, wherein the angle forms a defined cutting edge at an intersection of the end surface and a sidewall of the single-fiber thread.

12. The wound cleaning assembly of claim 1, wherein said wound cleansing cloth has four edges, and each edge is from 5 to 20 cm in length.

13. The wound cleaning assembly of claim 1, further comprising a pocket formed on a surface of the supporting layer facing away from the threads, wherein said pocket is adapted to engage a hand of a person using the wound cleaning assembly.

14. A method for treating acute or chronic wounds to remove substances formed by the body itself in the wound while preserving newly sprouting skin spots comprising:
    removing the wound cleansing cloth of claim 1 from the sealed packaging; and wiping the wound with the threads of the wound cleansing cloth.

* * * * *